(12) United States Patent
Zollorsch et al.

(10) Patent No.: US 11,340,522 B2
(45) Date of Patent: May 24, 2022

(54) DEVICE FOR HOLDING X-RAY FILMS

(71) Applicant: SICAT GMBH & CO. KG, Bonn (DE)

(72) Inventors: Andreas Zollorsch, Bonn (DE); Jiri Cizek, Garching (DE)

(73) Assignee: SICAT GMBH & CO. KG, Bonn (DE)

( * ) Notice: Subject to any disclaimer, the term of this patent is extended or adjusted under 35 U.S.C. 154(b) by 92 days.

(21) Appl. No.: 16/760,443

(22) PCT Filed: Oct. 24, 2018

(86) PCT No.: PCT/EP2018/079106
§ 371 (c)(1),
(2) Date: Apr. 30, 2020

(87) PCT Pub. No.: WO2019/086302
PCT Pub. Date: May 9, 2019

(65) Prior Publication Data
US 2020/0285141 A1    Sep. 10, 2020

(30) Foreign Application Priority Data
Nov. 3, 2017  (DE) .................... 10 2017 125 671.7

(51) Int. Cl.
*G06K 9/00* (2022.01)
*G03B 42/04* (2021.01)
(Continued)

(52) U.S. Cl.
CPC ............ *G03B 42/042* (2013.01); *A61B 6/145* (2013.01); *G06T 7/38* (2017.01); *B33Y 80/00* (2014.12);
(Continued)

(58) Field of Classification Search
CPC .................................................. G03B 42/042
See application file for complete search history.

(56) References Cited

U.S. PATENT DOCUMENTS 5,090,047 A   2/1992   Angotti et al.
5,113,424 A   5/1992   Burdea et al.
(Continued)

FOREIGN PATENT DOCUMENTS

JP         5-317307 A   12/1993

*Primary Examiner* — Oneal R Mistry
(74) *Attorney, Agent, or Firm* — Norman B. Thot

(57) ABSTRACT

A method for producing a holding apparatus for an x-ray film for teeth of a patient. The method includes performing an image registration of a first two-dimensional x-ray image of a tooth of an upper or lower jaw in a three-dimensional volume-tomographic data record of a jaw with a computer, determining a relative position of the first two-dimensional x-ray image within the three-dimensional volume-tomographic data record, preparing a virtual model for a holding apparatus that is attachable to the teeth of the upper or lower jaw in an interlocking fashion on the basis of the three-dimensional volume-tomographic data record, and producing the holding apparatus based on the virtual model. The holding apparatus includes a holding element which holds the x-ray film in a defined position. The defined position is established by the relative position of the first two-dimensional x-ray image in the three-dimensional volume-tomographic data record.

12 Claims, 3 Drawing Sheets

(51) Int. Cl.
    *G06T 7/38*      (2017.01)
    *A61B 6/14*      (2006.01)
    *B33Y 80/00*     (2015.01)

(52) U.S. Cl.
    CPC ............... *G06T 2207/10081* (2013.01); *G06T 2207/30036* (2013.01)

(56) References Cited

U.S. PATENT DOCUMENTS

| | | | |
|---|---|---|---|
| 5,625,666 A * | 4/1997 | Willis | G03B 42/042 378/170 |
| 7,204,640 B2 | 4/2007 | Fu et al. | |
| 2009/0162813 A1* | 6/2009 | Glor | A61C 1/084 433/196 |
| 2015/0327950 A1* | 11/2015 | Yao | A61C 7/02 433/3 |
| 2015/0359479 A1 | 12/2015 | Crandall et al. | |
| 2016/0262856 A1* | 9/2016 | Atiya | A61B 1/015 |
| 2016/0284241 A1* | 9/2016 | Silva | G09B 23/32 |
| 2018/0014747 A1* | 1/2018 | Akselrod | A61B 5/0531 |
| 2018/0017512 A1* | 1/2018 | Akselrod | A61C 13/30 |
| 2018/0122089 A1* | 5/2018 | Kim | A61B 6/4085 |
| 2020/0113654 A1* | 4/2020 | Akselrod | A61B 5/0031 |

\* cited by examiner

DEVICE FOR HOLDING X-RAY FILMS

CROSS REFERENCE TO PRIOR APPLICATIONS

This application is a U.S. National Phase application under 35 U.S.C. § 371 of International Application No. PCT/EP2018/079106, filed on Oct. 24, 2018 and which claims benefit to German Patent Application No. 10 2017 125 671.7, filed on Nov. 3, 2017. The International Application was published in German on May 9, 2019 as WO 2019/086302 A1 under PCT Article 21 (2).

FIELD

The present invention relates to a holding apparatus for x-ray films and to a method for producing the holding apparatus for x-ray films, as are in particular used during dental treatments by a dentist. An x-ray film is here held in the oral cavity by the holding apparatus while a diagnostic image is created. An x-ray film within the scope of the present invention also includes a digital sensor. Digital sensors are often used in dentistry instead of "conventional" x-ray films.

BACKGROUND

X-ray recordings of the teeth or the jaw of a patient are often recorded during a daily routine in dental practices to allow the dentist to make a diagnosis. A dental assistant thereby places the x-ray film in the oral cavity of the patient before the imaging diagnosis is started. If a plurality of image recordings are required during the scope of the treatment of the tooth and/or the jaw, a plurality of x-ray recordings must be made on different x-ray films, whereby the dentist is able to identify the course of the treatment and/or the course of the disease by comparing the various x-ray films. It is thereby disadvantageous that the diagnosis is made more difficult for the dentist because the x-ray films are only comparable to a limited extent since their position can vary greatly from recording to recording. The dental assistants do not introduce the x-ray films into the oral cavity at the same position during each recording, nor are the x-ray films attached at this point. The x-ray films can therefore change both in terms of their translation coordinates and their rotation coordinates prior to, and even during, the x-ray recording. The result of the findings can thus be falsified by virtue of, for example, a tooth being observed under different viewing angles in different x-ray films, thereby making comparability more difficult. There is thus an overall variability in the initial parameters.

U.S. Pat. No. 7,204,640 B2 describes an apparatus and a method that allow x-ray films to be registered to a digital volume-tomographic (DVT) data record in order to be able to determine how the x-ray film is disposed within the DVT data record. This method is, for example, used during patient positioning in radiotherapy. The treatment is usually planned by a DVT data record, for example, by a dose distribution during tumor irradiation, and the patient is then positioned based on 2D x-ray recordings which are made immediately prior to the treatment. In order to be able to position the patient at the correct position for the irradiation, it is necessary to ascertain where the 2D x-ray recordings are located within the DVT data record.

Numerous difficulties exist when placing an x-ray film and/or an x-ray sensor in the oral cavity of the patient since the positioning of the sensor in particular has many degrees of freedom: i.e., the position in the jaw arch, the rotation of the sensor about its axes and the bite of the patient on the sensor holder and/or film holder change the relative position of the sensor on the basis of specific tooth positions, underbite and/or overbite and bite pressure of the patient. All these uncertainty factors must be controlled in order to be able to reproducibly produce an x-ray image via an intraoral sensor so as to obtain improved comparability.

SUMMARY

An aspect of the present invention is to provide a method and an apparatus that allow different x-ray films to be recorded so that the x-ray films are created with the same initial parameters and are therefore comparable.

In an embodiment, the present invention provides a method for producing a holding apparatus for an x-ray film for teeth of a patient. The method includes performing an image registration of a first two-dimensional x-ray image of a tooth of an upper jaw or of a lower jaw in a three-dimensional volume-tomographic data record of a jaw with a computer, determining a relative position of the first two-dimensional x-ray image within the three-dimensional volume-tomographic data record, preparing a virtual model for a holding apparatus that is attachable to the teeth of the lower jaw or to the teeth of the upper jaw in an interlocking fashion on the basis of the three-dimensional volume-tomographic data record, and producing the holding apparatus based on the virtual model. The holding apparatus comprises a holding element which is configured to hold the x-ray film in a defined position. The defined position is established by the relative position of the first two-dimensional x-ray image in the three-dimensional volume-tomographic data record.

BRIEF DESCRIPTION OF THE DRAWINGS

The present invention is described in greater detail below on the basis of embodiments and of the drawings in which.

DETAILED DESCRIPTION

Figure 1:
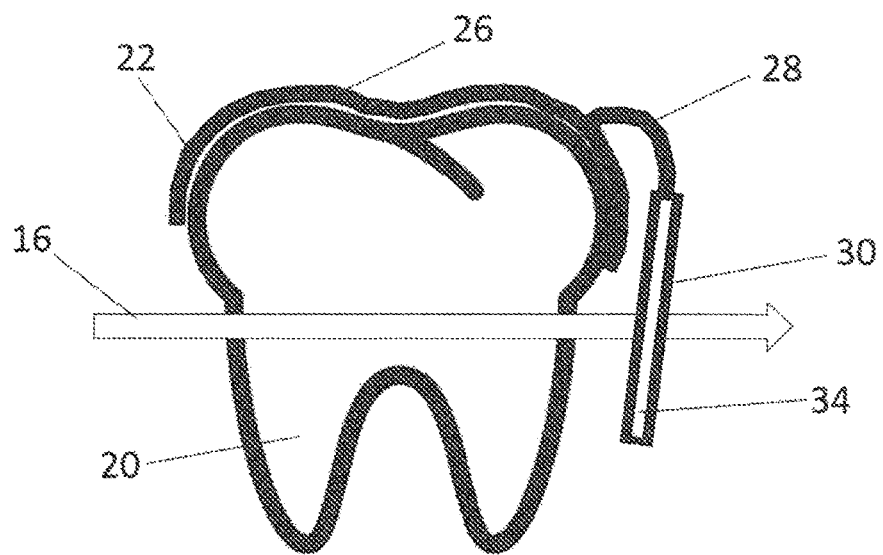
FIG. 1 shows a sectional illustration of a first schematic exemplary embodiment of a drill template according to the present invention with a holding element.

According to the present invention, a computer is used to perform an image registration of a first x-ray image, in particular an intraoral x-ray image, of a tooth of the upper or lower jaw in a digital three-dimensional volume-tomographic data record of the oral cavity in the method for producing a holding apparatus for x-ray films of a patient, wherein the relative position of the first x-ray image is determined within the volume-tomographic data record, and a virtual model for a holding apparatus that is attachable to the teeth of the lower or upper jaw in interlocking fashion is created on the basis of the volume-tomographic data record, the holding apparatus comprising a holding element for holding an x-ray film in a defined position, wherein the defined position is set by the relative position of the first x-ray image in the volume-tomographic data record and the holding apparatus is produced in accordance with the virtual model. An x-ray film within the scope of the present invention also comprises a digital sensor, which is often used in dentistry instead of "conventional" x-ray films. In order to further increase the quality and/or resolution of the volume-tomographic data record, digital tooth impressions, created using the CAD/CAM CEREC process, can be optionally fused with the volume-tomographic data record. In the CAD/CAM CEREC process, an optical imprint of the tooth or the teeth is scanned by an intraoral camera and a three-dimensional model is calculated. The three-dimensional model can be displayed and processed on a monitor and can be fused with the volume-tomographic data record.

The registration of the first intraoral x-ray image of a first x-ray film with the volume-tomographic data record advantageously achieves that the relative position of the first intraoral x-ray image is known within the volume-tomographic data record. Within the virtual model, the holding element is envisaged at this defined position so that a second x-ray film, which is introduced into the holding element and/or which is held thereby, is held at the same position during imaging as the first x-ray film. The holding apparatus is also attached to the teeth in an interlocking fashion to provide that the holding apparatus does not change its position during the imaging. The first x-ray film can therefore be conventionally created by a dentist, the first x-ray film easily being comparable to every further x-ray film held by the holding element. To calculate the interlocking property of the virtual model, the volume-tomographic data record or, alternatively, a plaster model that is subsequently digitized and fused with the volume-tomographic data record, is selectively used. The holding apparatus is alternatively designated as a template and/or tooth template or as a drill template. The term template takes account of the fact that the holding apparatus, i.e., the template, can also be used for further dental interventions since a drill channel can, for example, be provided in addition to the holding element. The registration can, for example, be implemented automatically and/or semi-automatically. This can also be understood to mean that the holding apparatus can also be created when a drill template is manufactured with hardly any additional outlay.

In an embodiment of the present invention, the holding apparatus can, for example, be produced on the basis of the virtual model and the defined position of the holding element in the volume-tomographic data record via a milling technique and/or via 3D printing. Both production methods facilitate a precise, reproducible and cost-effective production of the holding apparatus.

In an embodiment of the present invention, the holding apparatus can, for example, be manufactured from biocompatible material since the holding apparatus is used in the oral cavity of the patient and should ideally also be naturally degradable. The material should, where possible, not be opaque in relation to x-ray radiation.

In an embodiment of the present invention, the holding apparatus, in particular the holding element, can, for example, be produced from a homogenous material with an atomic number that is as low as possible. Homogenous properties provide that the x-ray radiation strikes each position on the film with equal intensity and therefore does not falsify the results due thereto. The attenuation of x-ray beams when passing through material depends on the material and is described by the Beer-Lambert law: $I=I0*exp(k*d)$, where I0 is the initial intensity, d is the path length, and k is a material-dependent coefficient which is proportional to the fourth power of the atomic number of the material through which the x-ray radiation passes. The material should thus, for example, have an atomic number lower than that of calcium, in particular since calcium is the primary interaction partner of the x-ray radiation in the human body. The dose of x-ray radiation would otherwise need to be greatly increased to the disadvantage of the patient in order to obtain the same blackening in the second x-ray film as in the first x-ray film. Materials that can be produced from hydrocarbon compounds are suitable.

The holding element advantageously has an embodiment that is as thin as possible in a transmission direction of the x-ray radiation, in particular at the points that cover the points in the oral cavity to be examined. The material thickness of the holding element can be thinner than 1 mm, for example, thinner than 0.75 mm, and in particular, for example, thinner than 0.5 mm in the transmission direction. At points connecting the holding element to the holding apparatus, the material strength should be provided so that the holding element is connected as rigidly as possible and in an immobile fashion to the holding apparatus so that no change in the defined position occurs. At these points, a material thickness of more than 1 mm, for example, more than 3 mm can, for example, be provided. Other points, in particular those serving to secure the x-ray film, may also require a thicker material strength of the holding element. The sections of the holding element covering the points on the teeth and/or in the jaw to be examined suitably have a material strength that is as thin as possible because otherwise, as explained above, the dose of the x-ray radiation would need to be increased in order to obtain the same degrees of blackening of the x-ray films as in the case without the holding element. The holding element is here provided in the style of a pocket into which the x-ray film can be inserted from above.

The holding element can alternatively have a U-shaped embodiment in the transmission direction for x-ray radiation, in particular at the points that cover the points in the oral cavity to be examined. Groove-like depressions can here be worked into the inner surfaces of the U-shaped form of the holding element, the x-ray film being insertable into the depressions from above. The holding element is here provided in the style of a frame. In this embodiment, the x-ray radiation is not attenuated since the points on the teeth or in the jaw to be examined are not covered by the material of the holding element. The x-ray film, as a result of being inserted from above, is secured in relation to the gravitational force in the U-shaped form.

The holding element alternatively comprises holding hooks which are attached to strategic positions in order to hold the x-ray film. Depending on the application, the x-ray film can be clamped by these holding hooks so that additional degrees of freedom, for example, a displacement of the projection area, are still possible, for example, in order to better identify the root.

In an embodiment of the present invention, the geometric dimensions of the x-ray film can, for example, be taken into account during the production of the holding element. X-ray films from different producers may have different geometric dimensions which must be considered when creating the virtual model and when manufacturing the holding element to provide that the corresponding x-ray film can be introduced onto the holding element and/or into the holding element so that the relative position of the x-ray film does not change during the imaging as this would, in turn, disadvantageously influence the comparability of the x-ray films.

The present invention also provides a holding apparatus which is produced according to the above-described method.

In an embodiment of the present invention, the x-ray film can, for example, be inserted into the holding element in an interlocking fashion. This provides that the x-ray film has no play and remains in its defined position.

In an embodiment of the present invention, the holding apparatus can, for example, have a tooth attachment in the form of a tooth template. The holding apparatus can thereby be easily placed on the teeth of the patient. Since the tooth attachment is matched to the surface of the teeth of the patient, the attachment achieves a detachable affixment of the holding apparatus.

In an embodiment of the present invention, the tooth attachment can, for example, be connected to the holding element via a bridge element. As a result of the bridge element, the holding element advantageously need not be worked directly into the "body" of the holding apparatus, but can also be disposed at a distance therefrom. This makes it easier both to realize the defined position and to introduce the x-ray film into the holding element. The bridge element is in particular advantageous for the U form of the holding element.

The present invention will be explained in greater detail below on the basis of exemplary embodiments under reference to the attached drawings.

The method leading to the production of the holding apparatus can proceed as follows:

A patient with radiculitis and an intraoral x-ray image meets a specialist following a referral from a dentist. The specialist wishes to examine the tooth 20 and/or the jaw in greater detail and creates a DVT data record in order to undertake endodontological planning and order a therapy/ drill template 26 therefor. The specialist also loads the intraoral x-ray image into software together with the DVT data record and, using a (semi-)automatic algorithm, registers the intraoral x-ray image to the point in the DVT data record at which the x-ray film was located as the image of the x-ray film was recorded. Apart from more precise findings, made available by fusing the intraoral x-ray image and the DVT data record, the specialist/consultant or the software now has available the spatial data of the x-ray film in relation to the head of the patient.

For the purposes of ordering a drill template 26, the specialist creates a digital dental impression of the jaw carrying the tooth 20 to be treated. The form of the dentition can alternatively also be extracted directly from the DVT data record. The specialist likewise registers the dental impression with the DVT data record of the patient. The specialist orders the drill template 26 and transmits the registration data (x-ray film and dental impression) and the associated x-ray and surface data to a laboratory. The laboratory creates the tooth-worn drill template 26, which is also referred to as holding apparatus 26 above, for the treatment. The laboratory also attaches a holding element 30 in the form of a pocket 30 to the tooth-carrying drill template 26, it being possible to introduce the x-ray film 38 into said pocket. The position of the pocket 30 is provided so that, when the patient wears the template on the teeth 20 provided therefor, the second inserted x-ray film 38 is situated in the same position where the first x-ray film was situated when the original first intraoral x-ray image was created.

Following the treatment, the dentist creates a second intraoral x-ray image of the treated tooth 20 by virtue of using the pocket 30 of the template 26. Since both the first x-ray film and the second x-ray film 38 were situated at the same position relative to the tooth 20 during the image recording, their respective x-ray images are easily comparable. All of this can be repeated multiple times by the specialist, or else the referring dentist, in order to assess the healing progress. Since the intraoral x-ray recording, as a projection, was always recorded in exactly the same way, the assessment of the course of healing is possible easier and quicker than where the x-ray films 38 from different positions need to be compared to one another.

The pocket 30 of the drill template 26 has here arisen as a byproduct of the actual treatment without the specialist having great additional work outlay. It is understood that the present invention is not restricted only to x-ray films 38, but that any sensor suitable for intraoral recording are also included under the present invention.

FIG. 1 shows a first schematic exemplary embodiment of the drill template 26 according to the present invention in a sectional illustration. In this case, a section of the drill template 26, which is placed on the tooth 20, is matched to a tooth surface 22 of the tooth 20 so that the drill template 26 is detachably affixed to the tooth 20. A bridge element 28 extends from the tooth-worn section of the drill template 26, the bridge element 28 being connected the pocket 30 for receiving the x-ray film 38. The bridge element 28 allows different spatial positions of the pocket 30 to be realized during the production in a simple manner. FIG. 1 also shows a transmission direction 16, which reproduces the preferred direction of the x-ray radiation during the imaging. Prior to the image recording, the second x-ray film 38 is introduced into the pocket 30, wherein the position of the pocket 30 replicates the relative position of the first x-ray film so that the second x-ray film 38 is situated in the same position relative to the tooth 20 as the first x-ray film.

Figure 2:
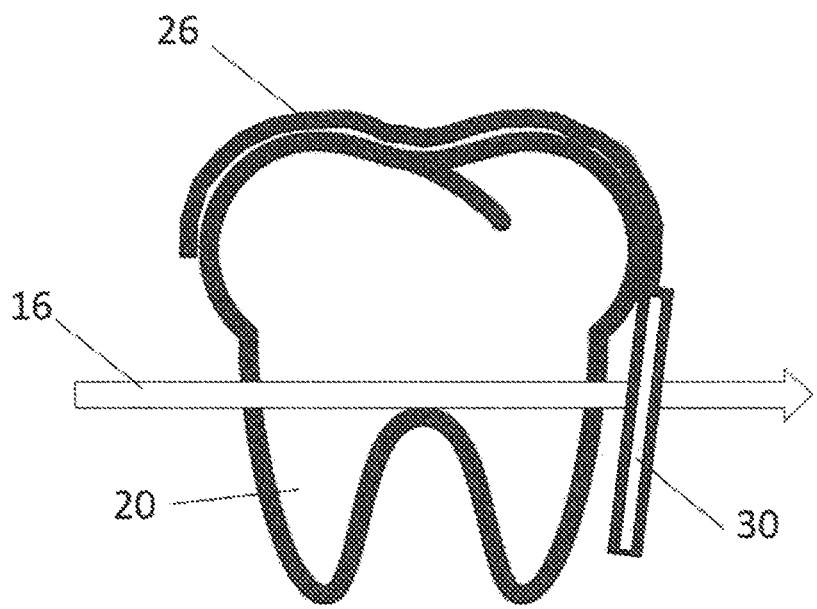
FIG. 2 shows a second schematic exemplary embodiment of the drill template according to the present invention from FIG. 1.

FIG. 2 shows a second exemplary embodiment of the drill template 26, wherein the pocket 30 is connected directly, and without the bridge element 28, to the drill template 26. The drill template 26 and the pocket 30 can, for example, be manufactured in an integral fashion both in the first exemplary embodiment and in the second exemplary embodiment.

Figure 3:
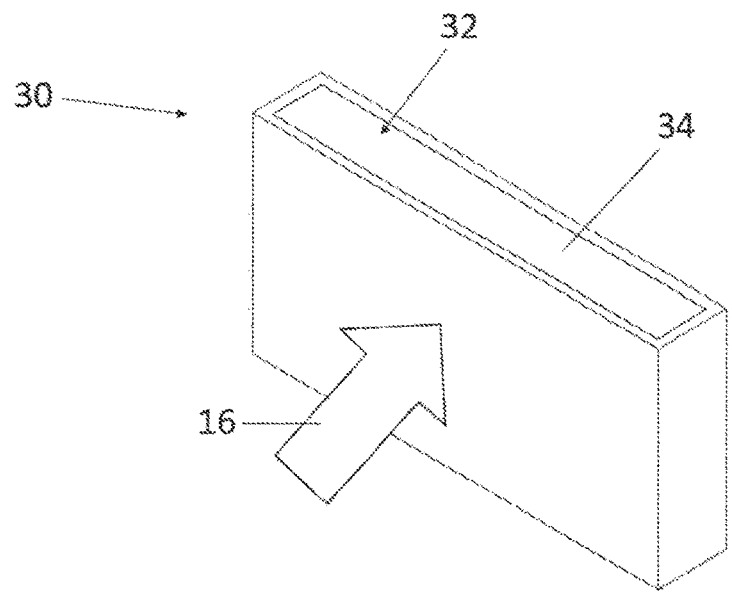
FIG. 3 shows a perspective illustration of the first exemplary embodiment of the holding element from FIG. 1 in the form of a pocket for receiving x-ray films.

FIG. 3 shows a perspective illustration of a first exemplary embodiment of the pocket 30 of the drill template 26 for receiving x-ray films. The form of the pocket 30 essentially corresponds to a rectangular hollow body with an opening 32 into which the x-ray film 38 is introducible. The opening 32 can, for example, be disposed on an upper side, wherein the upper side should be understood to be the side directed counter to the direction of gravity. This prevents the x-ray film 38 from inadvertently falling out of the pocket 30 as a result of gravity following the introduction into a recording space 34 (see FIG. 1). The pocket 30 consists of biocompatible material.

Figures 4, 5:
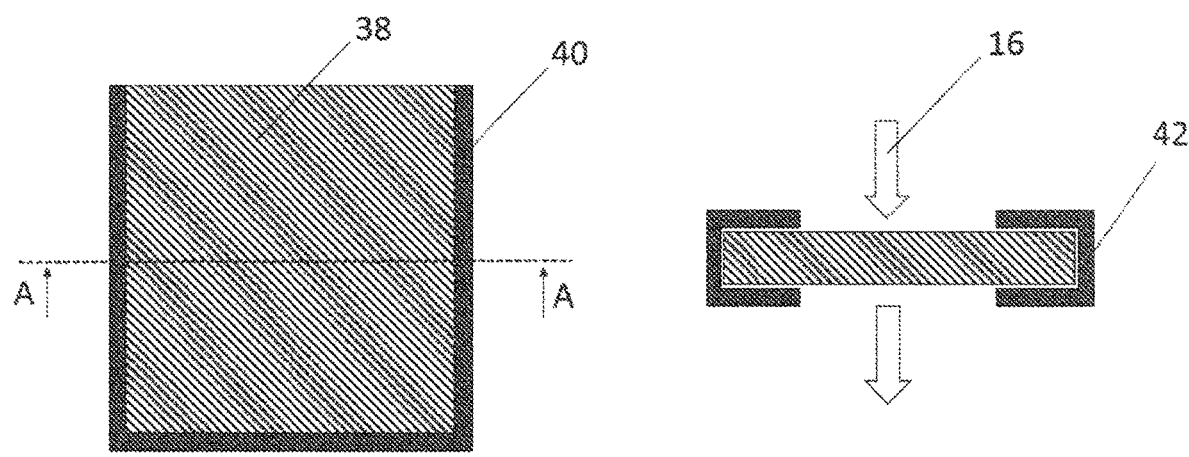
FIG. 4 shows a cross section along a transmission direction of the x-ray radiation of the second exemplary embodiment of the holding element from FIG. 3 in the form of a U-shaped frame.
FIG. 5 shows the holding element in a section through plane A from FIG. 4.

FIG. 4 shows, in a cross section along the transmission direction 16 of the x-ray radiation, a second exemplary embodiment of the holding element 30 of the drill template 26 from FIG. 3. Unlike what is shown in FIG. 3, the side surfaces of the holding element 30 in the transmission direction 16 no longer have an areal embodiment made of a material. The material much rather has the form of a U-shaped frame 40 in the transmission direction 16. This is advantageous in that the x-ray radiation can pass through the x-ray film 38 introduced into the recording space 34 without being attenuated by the material of the holding element 30.

FIG. 5 shows the holding element 30 in a section through the plane A of FIG. 4. What is shown here is that side receptacles 42 of the holding element 30 likewise have a U-shaped embodiment in a cross section, and so the x-ray film 38 can easily be inserted into the holding element 30.

Figure 6:
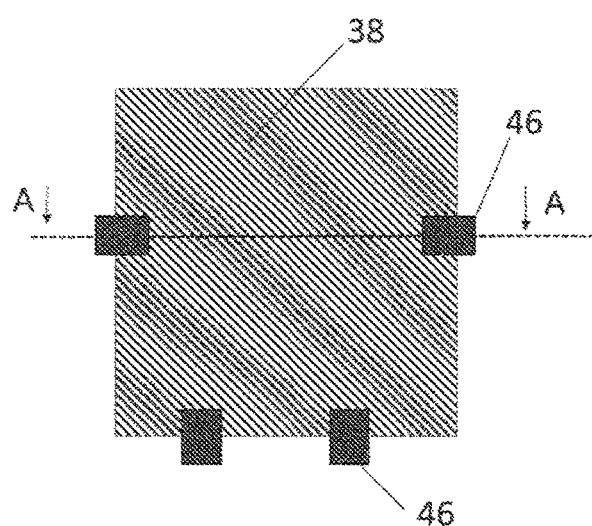
FIG. 6 shows, along a transmission direction of the x-ray radiation, a third exemplary embodiment of the holding element from FIG. 3 in the form of individual holding hooks.

FIG. 6 shows a cross section along the transmission direction 16 of the x-ray radiation of a third exemplary embodiment of the holding element 30 of the drill template 26 from FIG. 3. The material of the holding element 30 is further reduced in this exemplary embodiment so that the x-ray film 38 is held by holding hooks 46. The number of holding hooks 46 is in principle freely selectable as long as a "secure" hold of the x-ray film 38 is provided.

Figure 7:
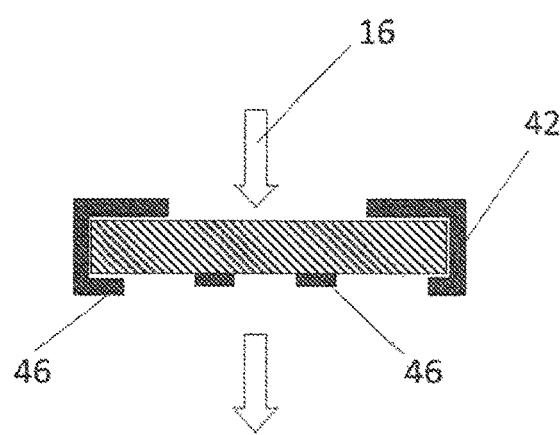
FIG. 7 shows the holding element in a plan view through plane A from FIG. 6.

FIG. 7 shows the holding element 30 including the holding hooks 46 in a plan view through the plane A from FIG. 6. FIG. 7 shows that the holding hooks 46 are connected to the lateral receptacle 42.

The present invention is not limited to embodiments described herein; reference should be had to the appended claims.

What is claimed is:

1. A method for producing a holding apparatus for an x-ray film for teeth of a patient, the method comprising:
    performing an image registration of a first two-dimensional x-ray image of a tooth of an upper jaw or of a lower jaw in a three-dimensional volume-tomographic data record of a jaw with a computer;
    determining a relative position of the first two-dimensional x-ray image within the three-dimensional volume-tomographic data record;
    preparing a virtual model for a holding apparatus that is attachable to the teeth of the lower jaw or to the teeth of the upper jaw in an interlocking fashion on the basis of the three-dimensional volume-tomographic data record, the holding apparatus comprising a holding element which is configured to hold the x-ray film in a defined position, the defined position being established by the relative position of the first two-dimensional x-ray image in the three-dimensional volume-tomographic data record; and
    producing the holding apparatus based on the virtual model.

2. The method as recited in claim 1, wherein the producing of the holding apparatus is performed via at least one of a milling method and a 3D printing method based on the defined position in the volume-tomographic data record.

3. The method as recited in claim 1, wherein the holding apparatus is made of a biocompatible material.

4. The method as recited in claim 1, wherein the holding apparatus is produced from a homogenous material which has a low atomic number.

5. The method as recited in claim 1, wherein the holding element is produced from a homogenous material which has a low atomic number.

6. The method as recited in claim 1, wherein the holding element is thinner than 1 mm in a transmission direction of x-ray radiation.

7. The method as recited in claim 1, wherein the holding element comprises a U-shape in a transmission direction of x-ray radiation.

8. The method as recited in claim 1, wherein geometric dimensions of the x-ray film are considered during the producing of the holding element.

9. A holding apparatus for teeth of a patient, the holding apparatus comprising:
    a holding element which is produced as recited in claim 1.

10. The holding apparatus as recited in claim 9, wherein the holding apparatus is configured so that the x-ray film can be inserted therein in an interlocking fashion.

11. The holding apparatus as recited in claim 9, wherein the holding apparatus comprises a tooth attachment.

12. The holding apparatus as recited in claim 11, wherein, the holding apparatus further comprises a bridge element, and
    the tooth attachment is connected to the holding element via the bridge element.

\* \* \* \* \*